United States Patent [19]

Shiuh

[11] 3,946,596

[45] Mar. 30, 1976

[54] LEAF FILTER TEST AND APPARATUS

[75] Inventor: Jerome Chung-Hsiung Shiuh, Englewood, Colo.

[73] Assignee: Johns-Manville Corporation, Denver, Colo.

[22] Filed: May 13, 1974

[21] Appl. No.: 469,491

[52] U.S. Cl. .................... 73/38; 73/61.2; 73/61.4; 73/63; 162/49; 162/198; 210/67
[51] Int. Cl.² .................. G01N 15/08; B01D 37/00
[58] Field of Search ............ 73/38, 61.2, 61.3, 61.4, 73/61 R, 63; 162/49, 198, 263; 210/66, 68

[56] References Cited
UNITED STATES PATENTS

| | | |
|---|---|---|
| 3,160,000 | 12/1964 | Mosher .............................. 73/61 R |
| 3,238,452 | 3/1966 | Schmitt et al. ...................... 73/61 R |
| 3,483,078 | 12/1969 | Sepall et al. ........................ 162/198 |
| 3,733,888 | 5/1973 | Danforth ............................... 73/63 |

Primary Examiner—Richard E. Aegerter
Assistant Examiner—Steven L. Stephan
Attorney, Agent, or Firm—Robert M. Krone; James W. McClain

[57] ABSTRACT

A simple and rapid test, and an apparatus for use therein, is described for measuring the filtration, or drainage, characteristics of a fibrous slurry. The results obtained by this test are accurately reproduced in production size systems, e.g. a wet process for the manufacture of asbestos-cement products such as sheet or pipe. The test utilizes a portable, light-weight leaf filter and can be run in 2–3 minutes.

4 Claims, 5 Drawing Figures

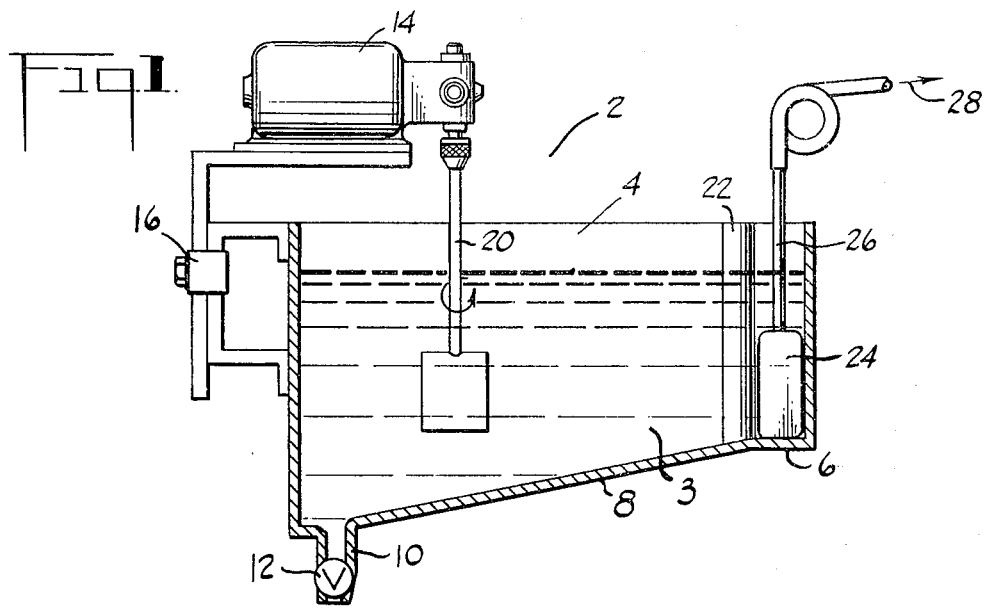
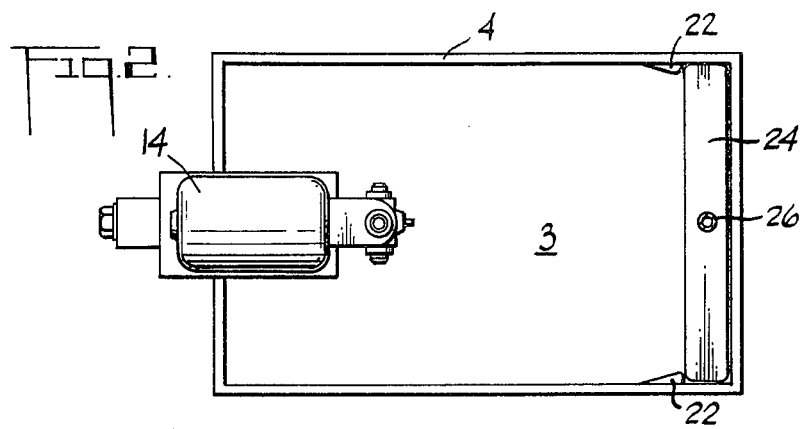
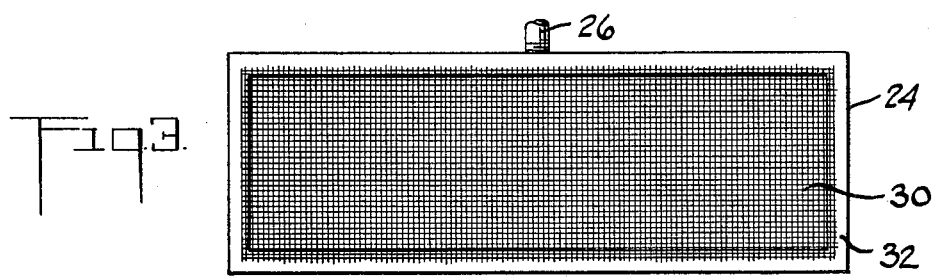
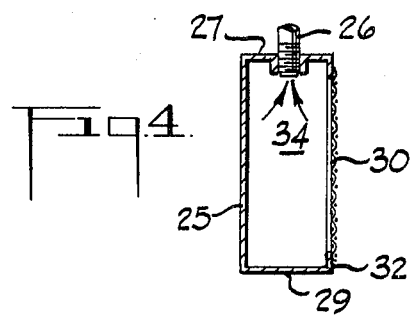

LEAF FILTER TEST AND APPARATUS

The present invention relates to a leaf filter test for determining the filtration, or draining characteristics of slurries containing fibers suspended therein, and an apparatus for performing the test.

BACKGROUND OF THE INVENTION

In research and development, and in the quality control, of fibrous slurries used for forming articles by drawing the liquid through a permeable member, having passages sufficiently small to prevent the solids in the slurry from passing therethrough, it is often desirable to determine the filtration, or drainage, characteristics of the slurry using only a relatively small slurry sample. By making an accurate determination on a small sample, undesirable slurry ingredients and/or slurry compositions can be detected and eliminated. Also, by testing slurries intended for use on a production unit, data is obtained that can be used to pre-set process parameters for each different slurry to reduce the amount of defective products produced. However, to accomplish these objectives it is essential that the results produced by the test accurately represent the results that the production unit will produce. The type of production units referred to here are disclosed in detail in numerous U.S. Pat. Nos., e.g. 2,182,353, 2,246,537, 2,322,592, 3,095,346 and 3,715,230.

The tests previously used to determine the drainage characteristics of slurries comprising asbestos fibers and hydraulic cement particles have failed to produce results that accurately represent the performance of the slurries in a production sized process or are too complex and require too much time to be practically useful. Several tests have been proposed and used, but each suffers one or more of the defects just described.

One test frequently used, a standard test used in the paper industry, is called the TAPPI test. In this test, a fixed volume of slurry is poured into a graduated transparent cylinder having a 60 mesh (U.S. STD.) screen located in its bottom. The time required for a fixed volume of the liquid carrier to pass through the screen, under the influence of gravity and the slurry head in the cylinder, is measured to determine the drainage characteristics of the slurry. The results obtained using this test on slurries containing asbestos fiber are frequently not representative of the results found when the slurries are used in production sized wet process equipment for making asbestos/cement sheets, pipe, etc.

Another test, called the Alpharater test, is similar to the TAPPI test, except a partial vacuum of 200 mm of mercury is established on the down stream side of the 60 mesh screen. Like the TAPPI test, this test produces results that are not representative of those obtained on production sized wet machines.

A third test that has been used is called a Fiberator test. This test is similar to the Alpharater test, except that the screen area used is larger and the slurry head above the screen is smaller. In addition to measuring the filtrate volume, the weight of the layer of solids built up on the 60 mesh screen, in a fixed period of time, is also determined. While this test produces results that more closely approximate the results obtained on production sized equipment, this test is complicated and requires more time than desired.

The object of the present invention is to provide a test, and accompanying apparatus, that is simple, fast, and that produces results that will be representative of production sized equipment.

BRIEF SUMMARY OF THE INVENTION

The present invention provides a test method for determining the filtration, or drainage, characteristics of a fibrous slurry. The method comprises placing a small filter leaf into a fibrous slurry, connecting the interior of the filter leaf to a partial vacuum to remove liquid from the slurry and to deposit solids from the slurry onto the filter surface, removing the filter leaf after a fixed time from the slurry and allowing the partial vacuum to draw air through the layer of solids built up on the filter surface to remove any excess liquid therein, removing the layer of solids from the filter leaf, drying the layer and determining the weight of the dried layer. The production rate, or filtration rate, is then calculated using the following formula:

$$FR = \frac{DC}{FT \times SA}$$

where $FR$ = filtration rate in $gm/min/ft^2$, $DC$ = dry cake weight in grams, $FT$ = filtration time in minutes, and $SA$ = screen area in square feet.

The present invention also provides, in combination, a portable leaf filter means, a vacuum source means, and container means for running the above test. Optionally, agitation means can also be provided to prevent the solids in the slurry from settling.

BRIEF DESCRIPTION OF THE DRAWINGS

FIG. 1 is a cross sectional side view of a preferred apparatus for running the test of the present invention.

FIG. 2 is a plan view of the apparatus shown in FIG. 1.

FIG. 3 is a front view of a preferred leaf filter means.

FIG. 4 is a cross sectional view of the leaf filter shown in FIG. 3.

DETAILED DESCRIPTION AND PREFERRED EMBODIMENTS

Figure 5:
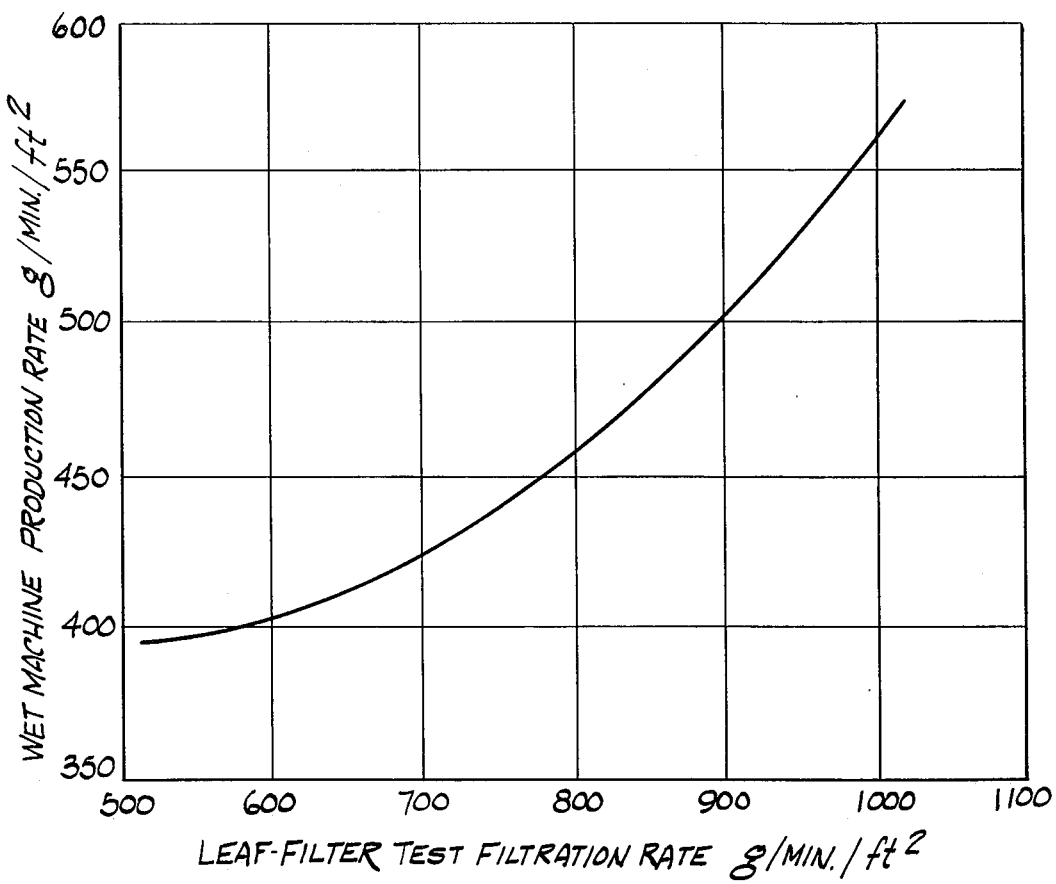
FIG. 5 is a graph showing the filtration rate of asbestos/cement slurries determined by the test of the present invention versus the filtration rate of the same slurries on production sized wet machines.

The leaf filter means is the key element in the apparatus and test of the present invention. It can be made in many shapes including a square box, rectangular box, a cylinder, etc. A preferred form is shown in FIGS. 3 and 4. The preferred form is a long rectangular box 24, preferably made from a rust resistant metal such as stainless steel or aluminum. A hole is cut in one of the large faces of the box leaving a flange 32 around the outer periphery. A rust resistant screen 30, preferably a 60 mesh (U.S. STD) stainless steel screen, is attached to the flange 32 by appropriate means, such as an adhesive or solder. A preferred size for the leaf filter screen opening is 5 by 2 inches. One of the walls 25, 27 or 29, preferably 27, is drilled and a fitting 26 is attached for connection to a vacuum source 28 for pulling liquid 34 from the slurry 3 through screen 30 and out through fitting 26.

This preferred leaf filter is light weight and portable, and therefore can be used for running a test in any container capable of holding a slurry, including the wet box of a forming apparatus used in the conventional wet forming process. A preferred apparatus for running bench tests using the test method of the present invention is shown in FIGS. 1 and 2. This apparatus 2 comprises a container 4, perferably having an inclined bottom surface 8 with a drain 10 and an on-off valve 12 for ease in removing the slurry and cleaning the container after the test is completed. The container 4 also has a short flat bottom section 6 and keeper means 22 for holding the leaf filter 24 in a constant position. The leaf filter 24 is placed in container 4 such that the screen 30 is exposed to the slurry 3.

Optionally, the container 4 can be provided with agitation means to prevent the solids in the slurry from settling. However, since the filter leaf is only in the slurry for a matter of seconds this is usually not necessary. As shown in FIGS. 1 and 2, an electric motor and drive 14 are mounted on container 4 by mounting means 16. A shaft 20 having an agitator blade 18 is rotated by the motor and drive 14 to provide agitation.

To run the test of the present invention using the apparatus shown in FIGS. 1 and 2 a slurry 3 is poured into container 4 until the slurry reaches a predetermined level. The agitation motor and drive means 14 are started. The leaf filter means is attached to a vacuum source 28, preferably about 200mm of mercury, and placed into the container 4, in the position shown in FIG. 1, and allowed to remain there for a predetermined time, preferably about 10 seconds. At the end of the predetermined time the filter leaf 24 is quickly withdrawn from container 4 and held in the air to allow the vacuum to pull excess moisture from the layer of solids built up on screen 30. The filter leaf 24 is then disconnected from the vacuum source 28 and the layer of solids is carefully peeled away from screen 30. Usually this layer of solids will have well defined dimensions equal to the screen area communicating with the interior of filter leaf 24. The layer of solids is then dried to constant weight and the weight is recorded. The filtration rate of the slurry can then be determined from the recorded data using the formula disclosed earlier in the specification.

It can readily be seen, due to the size and weight of the filter leaf used and the short time that the filter leaf is submerged in the slurry, that this test technique readily lends itself to use in any type of container. including process equipment such as slurry mixers, holding tanks, and wet boxes of forming machines. Depending on the type of dryer used, the entire test can be completed in as little time as 2–3 minutes. Therefore, the test is not only a useful laboratory test, but can also be used for quality control purposes in manufacturing operations.

The level of vacuum used in the preferred embodiment disclosed above, the screen size and shape used in the leaf filter, and the time that the filter leaf is submerged in the slurry, can all be changed substantially to accommodate different slurry compositions and conditions. For example, if a very low solids content slurry is being tested, it might be desirable to increase the submersion time of the filter leaf. Also, it is usually desirable to use a magnitude of vacuum equal to the magnitude on the production equipment for which the slurry is being tested.

FIG. 5 shows a curve worked out for asbestos/cement slurries prepared to produce different filtration, or production rates on a wet machine production unit. Each of these slurries was tested on both the production wet machine and the filter leaf of the present invention. The curve represents the filtration rates on the production unit versus the production rates on the leaf filter of the present invention. This curve is used to determine the production rate that can be expected on this production unit using the leaf filter rate determined on any asbestos/cement slurry. For example, if the leaf filter test of the present invention produced a production rate of 900 gm/min/ft$^2$ for a particular asbestos/cement slurry, one could determine the expected production rate on the production size machine by drawing a vertical line from 900 on the abscissa until it intersected the curve shown in FIG. 5. A horizontal line is then drawn from this intersection to the ordinate on the graph. The expected production rate is marked by the intersection of the horizontal line with the ordinate. If any variable of the test is changed, such as the machine size, the magnitude of the partial vacuum, or the submersion time of the filter leaf in the slurry, it would be necessary to establish a new curve.

It might be possible to eliminate the use of the curve shown in FIG. 5 by adjusting the parameters of the test, e.g., screen size, magnitude of partial vacuum, etc., to produce filtration rates approximately equal to those produced by production sized wet machines, but this is unnecessary since the curve in FIG. 5 is easy to use and provides sufficiently accurate results.

While the present invention has been described primarily with respect to an asbestos/cement slurry, the filter leaf test could be used on any fibrous slurry, e.g. slurries containing glass fibers, ceramic fibers, resin fibers, etc.

What I claim is:

1. A method for rapidly determining the filtration rate of a fibrous slurry comprising submerging a filter leaf a predetermined distance below the top surface of the slurry for a predetermined time, connecting the filter leaf to a predetermined level of magnitude of partial vacuum during the time the filter leaf is submerged in the slurry, withdrawing the filter leaf from the slurry at the end of said time, removing a layer of solids built up on the filter leaf, drying said layer of solids, and determining the drainage characteristics of the slurry according to the following formula:

$$FR = \frac{DC}{FT \times SA}$$

where $FR$ = filtration rate in gm/mm/ft$^2$, $FT$ = filtration time in minutes, $SA$ = screen area in square feet, and $DC$ = dry cake weight in grams.

2. The test method according to claim 1 wherein said fibrous slurry comprises water, asbestos fibers, and hydraulic cement particles.

3. An apparatus for determining the drainage characteristics of a fibrous slurry comprising container means for containing the slurry at a predetermined level, agitation means to agitate said slurry a filter leaf for collecting a layer of solids contained in said slurry, and a partial vacuum source for pulling liquid contained in said slurry out of said container and into and out of said filter leaf, said filter leaf comprising a container having an outlet for attachment to said partial vacuum source and another larger outlet covered by a permeable screen, said filter leaf being located in said container in an operative mode such that said larger outlet is located below said predetermined level thus placing said permeable screen in direct contact with an agitated portion of said slurry and therefor giving more reliable indication of the drainage characteristics of the slurry.

4. The apparatus of claim 3 wherein said filter leaf is a rectangular shaped box having an opening in a large face, said opening being covered by said permeable screen.

* * * * *